United States Patent [19]

Sickinger et al.

[11] Patent Number: 5,763,278
[45] Date of Patent: Jun. 9, 1998

[54] AUTOMATED PIPETTING OF SMALL VOLUMES

[75] Inventors: Anselm Sickinger, Greifensee; Johannes Konrad Balmer, Wetzikon, both of Switzerland

[73] Assignee: Tecan AG, Hombrechtikon, Switzerland

[21] Appl. No.: 551,325

[22] Filed: Nov. 1, 1995

[51] Int. Cl.$^6$ ..................................................... G01N 1/10
[52] U.S. Cl. ........................ 436/180; 436/179; 422/100; 422/103; 73/864.01; 73/863.32; 73/863.44; 73/864.13
[58] Field of Search ........................................ 422/100, 103; 436/179, 180; 73/863.32, 863.44, 864.01, 864.02, 864.12, 864.13

[56] References Cited

U.S. PATENT DOCUMENTS 3,798,961   3/1974   Flambard et al. .................... 73/71.5
4,223,558   9/1980   Schmider et al. ................... 73/421 R

*Primary Examiner*—Harold Y. Pyon
*Attorney, Agent, or Firm*—Walter C. Farley

[57] ABSTRACT

A device for automated pipetting of small volumes of liquid has a pipetting needle, a diluter having a liquid output with a syringe and a valve, the syringe including a piston and a piston drive. Tubing interconnects the needle and the liquid output of the diluter, the tubing and diluter containing a substantially incompressible liquid. An impulse generator is connected in the device and coupled to the incompressible liquid in the tubing for generating and applying directly to the liquid in the tubing a mechanical impulse force of at least 0.01 N·s for separating liquid from the needle.

17 Claims, 3 Drawing Sheets

AUTOMATED PIPETTING OF SMALL VOLUMES

FIELD OF THE INVENTION

This invention relates to a device for automated pipetting of small volumes of liquid in particular to volumes smaller than 10 μl.

BACKGROUND ART

Handling of volumes smaller than 10 μl requires adjusted instruments, and most frequently, in addition new techniques of pipetting. Volumes larger than 10 μl can easily be dispensed from the air, as the drops can leave the tip by themselves if handled appropriately. For volumes smaller than 10 μl techniques have to be applied that guarantee the emission of the droplets. For this reason, the tip can touch the wall of a vessel containing the liquid to be treated or the droplet can be dispensed directly into the desired liquid. A subsequent mixing step is advantageous in order to obtain a complete transfer. A third possibility, that is frequently used, is the pre-uptake of a reagent, which is finally dispensed together with the sample volume.

For the manual pipetting of low volumes, most frequently disposable tips are used in order to eliminate "carry over" (contamination), which necessarily occurs during the contact of the tip with other materials.

Two types of tips are used so far for the reproducible and exact pipetting of low volumes: the so-called "air-displacement tip" and the "positive-displacement tip", which is the more reliable one. The air-displacement tip is a normal disposable tip, which is adjusted to the low volume with respect to material and geometry. For the "positive-displacement tip" a piston is used inside of the tip in order to improve the accuracy.

For the automation of the pipetting process of small volumes two actions have to be distinguished: the defined aspiration of the liquid and the subsequent dispense. In between is the movement of either the arm of the operator or the device of the robot, that transfers the liquid.

Without this transfer, solely the liquid system consisting of diluter, tubing and tip is responsible for the accuracy. Especially the diluters are of significant importance.

A variety of diluters is commercially available, one of them the "CAVRO XL 3000 Modular Digital Pump" is marketed by Cavro Scientific Instruments Inc., Sunnyvale, Calif. Basically a diluter consists of a stepper motor-driven syringe pump for precision liquid handling. The diluter operates from a single 24 volt power supply and is controlled by an external computer or microprocessor. It works as slave unit automating pipetting, diluting and dispensing functions. Further particulars of this diluter are described in the Operator's manual P/N 724043C of Cavro Scientific Instruments Inc.

Known diluters have been developed that can aspirate and dispense volumes in the amount of nanoliters, at least in theory.

The movement of the plunger of the syringe of the diluter which is responsible for the volume has to affect the tip in order to obtain pipetting. For this reason the tubing usually is filled with liquid (system liquid, most frequently distilled water) which can be less easily compressed than air. This guarantees a reproducible handling of the moves.

The accuracy (ACC) and reproducibility (CV) of the pipetting can be influenced by various parameters. The most important one is the velocity of the aspiration and the dispense of the liquid. Diluters used so far are adapted to handle volumes of 10 μl with the appropriate resolution and velocity. However, the most critical point is the tearing off of the liquid from the tip, which is limited by the mechanics of the diluter.

Speed of the drive can not be increased infinitely. Even the speed that is required to dispense low volumes has not yet been reached.

For the pipetting of volumes smaller than 10 μl under usual conditions the limits are within the volume of one drop. The forming, the shape and the size of a drop primarily depends on the surface tension of the liquid, which results from the chemical and physical properties of the sample of the pipetted liquid.

The size of a drop of water is 10–20 μl, which is disadvantageous for the pipetting, because this is the minimum volume, that can be torn off from the tip. This effect becomes visible while attempting to pipette volumes of 1 μl: after 12–15 times of dispense, the drop has reached the critical size and is emitted.

However, there do exist applications of the dispensing of tiny droplets in the amount of nanoliters, for example in ink jet printers. In this case the droplets are shot with a piezo element. However, this technique is not suitable to cover the whole range of volumes required for the automated pipetting. Up to now, none of the developed techniques (diluter, piezo technic) successfully unify the advantages of each.

SUMMARY OF THE INVENTION

The invention is aimed at allowing the reproducible automated pipetting of small volumes of liquid, in particular to volumes smaller than 10 μl.

The combination of a state of the art diluter system with an impulse generator allows to shifting the physical/chemical limits of the forming of drops to lower volumes in the region below 10 μl.

The impulse generator can be put somewhere within the liquid system and the kind of generator that is used is of minor importance. The only pre-condition is that the generator is located between the valve of the diluter and the tip, or is built into the valve, or affects the plunger drive of the diluter so that it acts directly on the liquid.

In this system the advantages of a high efficacy diluter for the accurate measurement of the volume are further improved by the addition of an impulse generator, which allows the "break off" of low volumes. Now, the so far impossible, accurate and reproducible aspiration and dispense of low volumes can be handled with pipette robots, without the difficult techniques of exact positioning (which are also required in manual pipetting).

The invention allows the dispensing of low volumes from air.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

DETAILED DESCRIPTION OF THE INVENTION

Figure 1:
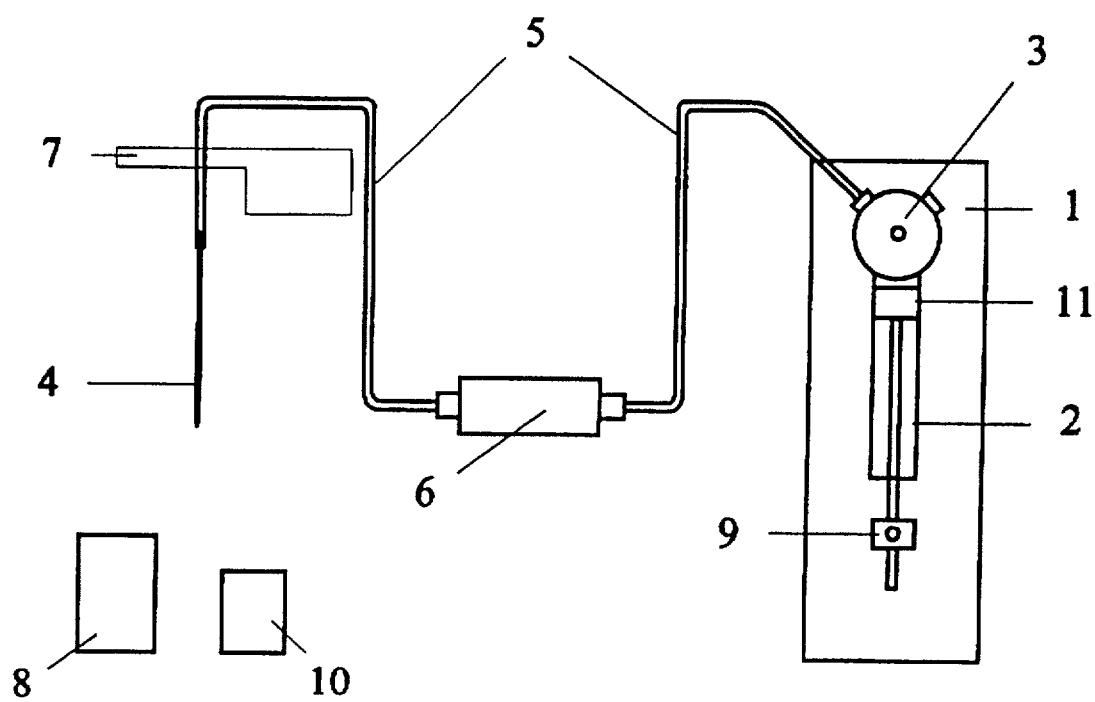
FIG. 1 is a schematic view of the device according to the invention.

The device shown in FIG. 1 basically consists of a diluter 1, a pipetting needle 4, a tubing 5 connecting said diluter 1 with said needle 4, and an impulse generator 6.

The diluter 1 comprises a syringe 2 and a valve 3, whereby said syringe 2 comprises a piston 11 and a piston drive 9. The impulse generator 6 is located between the valve 3 of said diluter 1 and said needle 4. Alternatively the impulse generator 6 can either be located in said valve 3 or on said piston drive 9.

The operation of the device according to the invention is described now in more detail:

At the very beginning the whole device is filled up with the appropriate system liquid, e.g. deionized water, a buffering solution or an oil.

A robot arm 7 moves needle 4 to the source 8, e.g. an open container with the liquid sample to be analyzed. After detection of the surface of this liquid by the needle 4 and submerging it some tenths of millimeters into said liquid the predetermined amount or volume of liquid sample is aspirated from the source 8 with a definable additional "conditioning" volume of the liquid sample through the needle 4 by means of the diluter 1. After retracting needle 4 out of the source 8 the "conditioning" volume is dispensed back into the source 8 by means of the diluter 1. This is effected by applying an equivalent number of steps of the piston drive 9 corresponding to the "conditioning volume".

Figures 2, 3, 4, 5:
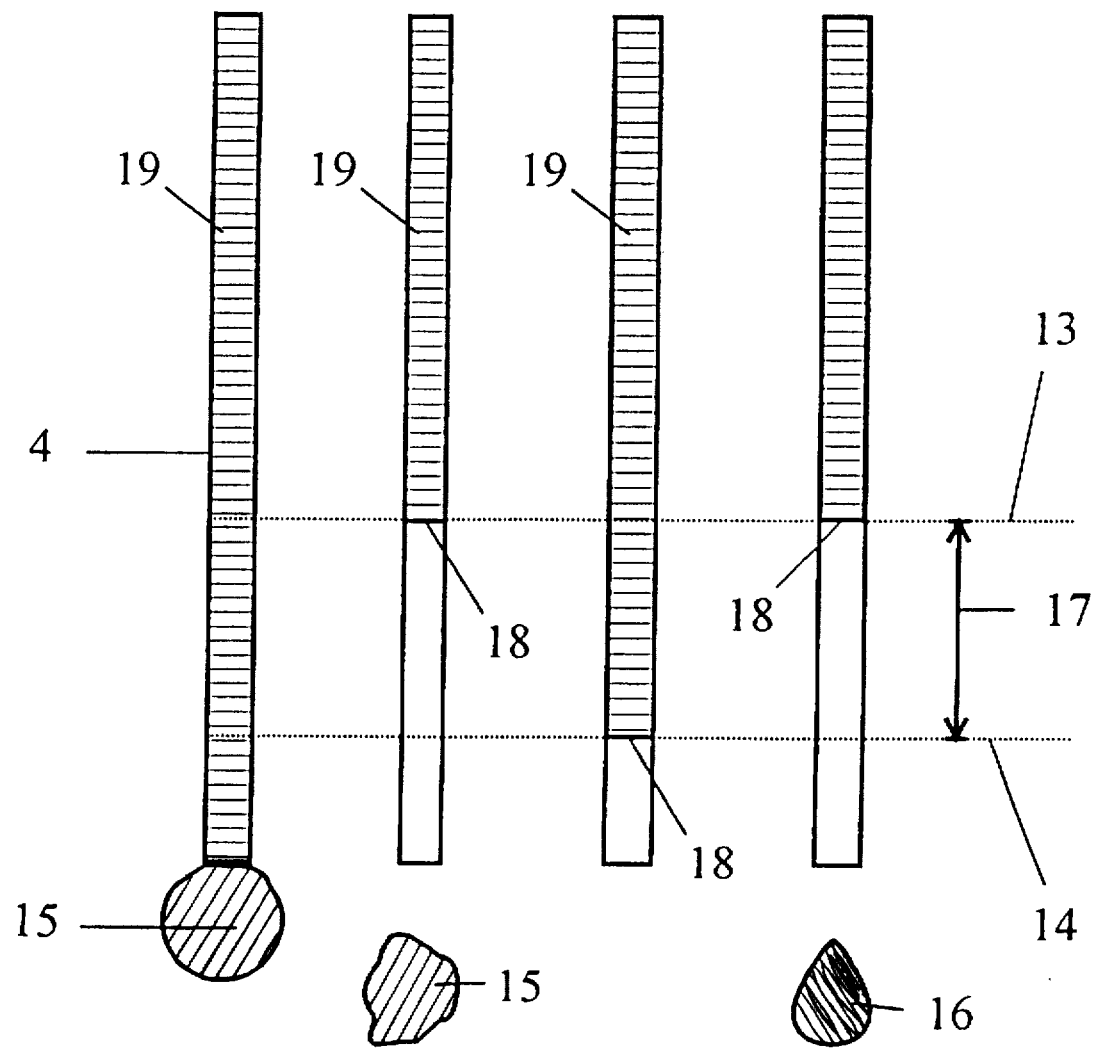
FIG. 2 is a schematic view of the needle of the device according to the invention before calibration of the device.
FIG. 3 is a schematic view of the needle of FIG. 2 after applying an impulse.
FIG. 4 is a schematic view of the needle of FIG. 3 after supplying a defined volume of liquid to the liquid column in the needle.
FIG. 5 is a schematic view of the needle of FIG. 4 after applying an impulse.

After this dispensing procedure the tip of the needle 4 is either dropless or has—as shown in FIG. 2—a drop of undefined volume 15, depending from the physico-chemical properties of the liquid used In the device. The pipetting needle 4 has an internal diameter smaller than 0.6 mm at its free end and preferably smaller than 0.4 mm.

Right after these movements of the diluter's piston 11 moved by the piston drive 9 the impulse generator 6 applies a force directly to the liquid column in the tubing 5 to grade the remaining liquid in the pipetting needle 4. The effect is—as shown in FIG. 3—that the meniscus 18 of the liquid resides inside of the tip 4 at a level 13 that only depends of the magnitude of the impulse generated by the impulse generator 6 and the transmission of said impulse to the liquid 19 in the tubing 5.

After moving needle 4 to the destination 10 (FIG. 1), e.g. an open container, the diluter 1 delivers the volume to be dispensed to the liquid in the tubing 5. As shown in FIG. 4 the meniscus 18 of the liquid 19 moves a distance (indicated by arrow 17) within the needle 4 to the level 14 and the impulse generator 6 again applies the impulse. The effect is—as shown in FIG. 5—that the volume delivered by the diluter 1 (liquid column between levels 13 and 14) breaks away from the tip of needle 4 in the form of drop 16 and the meniscus 18 of the liquid 19 inside the needle 4 comes to stop at the steady location at level 13 prior to the delivery of the liquid volume corresponding to drop 16. This procedure is applicable to both pipetting modes, single and multi pipetting (aliquotting).

The steady location of meniscus 18 at level 13 depends primarily upon the stroke of the impulse generator 6 and secondarily upon the magnitude of the impulse generated by impulse generator 6. If constant stroke and impulse are applied to the liquid 19 the location of the meniscus 18 will always be at the steady location at level 13.

The impulse generator 6 can be either a mechanical impulse generator (e.g. a core magnet or a solenoid pinch valve), or an inductive impulse generator, e.g. a piezo element. The impulse generator 6 can also comprise an ultrasonic source, or a heat source.

The magnitude of the impulses J generated by the impulse generator 6 should be in the order of 0.01 to 1.00 Newton× seconds (N·s), preferably in the order of 0.01 to 0.10 N·s. The variation of the magnitude of the impulse can be achieved by altering the controlling conditions of the impulse generator 6.

The syringe 2 of the diluter 1 has a volume in the range of 10 –500 μl. Preferably the volume is in the range of 100–400 μl and typically in the range of 200–300 μl. These indications are related to a pipetting volume in the range of 1–10 μl. The resolution of the diluter 1 is in the range of 3000 to 24,000 steps per full stroke.

The tubing 5 has an internal diameter of 0.1–1.0 mm and the pipetting needle 4 has an internal diameter smaller than 0.6 mm at its free end and preferably smaller than 0.4 mm. The pipetting needle 4 is coated externally with teflon, paraffin or fat or is silanized. The coating produces a hydrophobic surface which results in a more precise break-off of the liquid from the tip of the needle 4.

Figure 6:
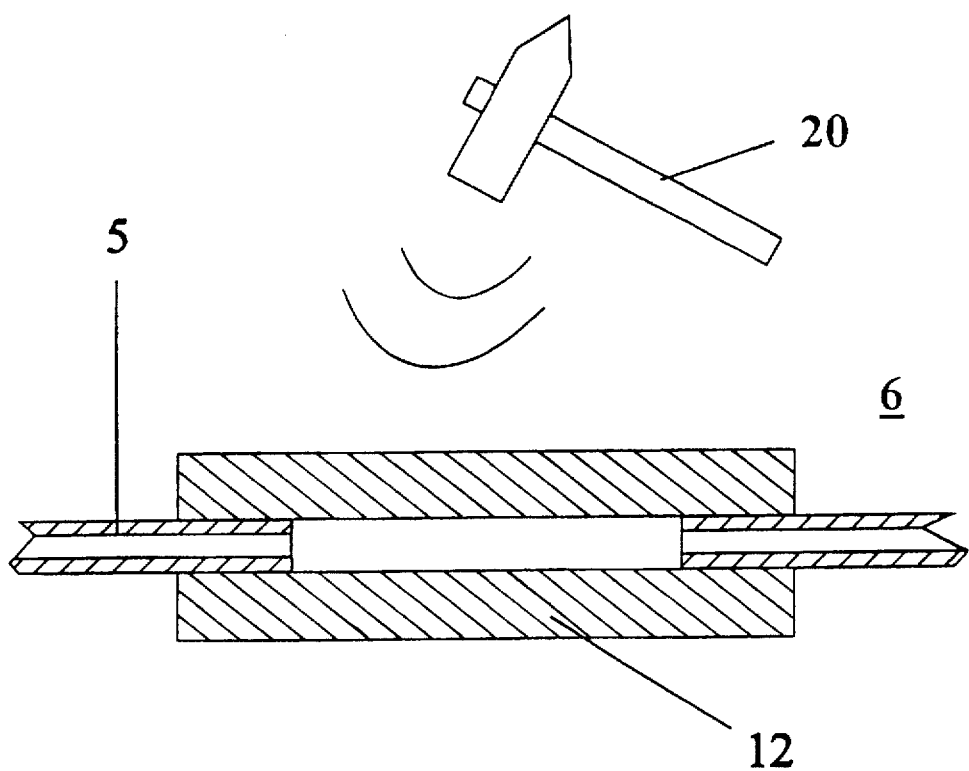
FIG. 6 is a longitudinal section through the impulse generator of FIG. 1.

As shown in FIG. 6 the portion 12 of said tubing 5 located within said impulse generator 6 is made of a different material then the tubing 5. Whereas the tubing 5 is generally made of polytetrafluorethylene (PTFE) the portion 12 is made of silicone. The application of the impulse indicated by hammer 20 on said portion 12 made of silicone gives optimum results. Tubing 5 has an internal diameter of 0.1–1.0 mm.

While the foregoing description and drawings represent the preferred embodiments of the present invention, it will be obvious for those skilled in the art that various changes and modifications may be made therein without departing from the true spirit and scope of the present invention.

We claim:

1. A device for automated pipetting of small volumes of liquid comprising a pipetting needle; a diluter having a liquid output and comprising a syringe and a valve, said syringe including a piston and a piston drive;

tubing interconnecting said needle and said liquid output of said diluter, said tubing and diluter containing a substantially incompressible liquid; and an impulse generator connected in said device and coupled to said incompressible liquid in said tubing for generating and applying directly to said liquid in said tubing a mechanical impulse force of at least 0.01 N·s for separating liquid from said needles, said impulse generator being selected from the group consisting of core magnet, a solenoid pinch valve, an inductive impulse generator, an impulse generator including a piezo element, an ultrasonic source and a heat source.

2. A device according to claim 1 wherein said impulse generator is located between said valve and said needle.

3. A device according to claim 1 wherein said impulse generator is located in said valve.

4. A device according to claim 1 wherein said impulse generator generates an impulse having a momentum in the range of 0.01 to 0.1 N·s.

5. A device according to claim 1 wherein said diluter has a resolution of 3,000 to 24,000 steps per full stroke.

6. A device according to claim 1 wherein said tubing comprises polytetrafluorethylene (PTFE).

7. A device according to claim 1 wherein a portion of said tubing inside of said impulse generator comprises silicone.

8. A device according to claim 1 wherein said tubing has an internal diameter of between 0.1 and 1.0 mm.

9. A device according to claim 1 wherein said needle has an internal diameter smaller than 0.6 mm at its distal end.

10. A device according to claim 9 wherein said needle has an internal diameter smaller than 0.4 mm at its distal end.

11. A device according to claim 1 wherein said pipetting needle comprises an external hydrophobic coating.

12. A device according to claim 11 wherein said coating is selected from the group comprising teflon, paraffin, fat or a silanized coating material.

13. A device according to claim 1 wherein said syringe has a volume in the range of 10 to 500 ml.

14. A device according to claim 13 wherein said syringe has a volume in the range of 100 to 400 ml.

15. A device according to claim 14 wherein said syringe has a volume in the range of 200 to 300 ml.

16. A method for automated pipetting of small volumes of liquid comprising providing a diluter having a liquid output and comprising a syringe and a valve, the syringe including a piston and a piston drive, interconnecting the output of the diluter to a pipetting needle with tubing, the tubing and diluter containing a substantially incompressible liquid, and forming a liquid column in said needle; and coupling an impulse generator to said incompressible liquid in said tubing and applying directly to said liquid in said tubing a mechanical impulse force of at least 0.01 N·s for separating liquid from said needle, said impulse generator being selected from the group consisting of a core magnet a solenoid pinch valve an inductive impulse generator, an impulse generator including a piezo element, an ultrasonic source and a heat source.

17. A method according to claim 16 wherein said liquid column has a defined volume smaller than 10 µl.

* * * * *